(12) United States Patent
Sauer et al.

(10) Patent No.: US 7,932,292 B2
(45) Date of Patent: Apr. 26, 2011

(54) USE OF QUATERNARY AMMONIUM COMPOUNDS IN THE REMEDIATION OF MOLD, MILDEW, AND FUNGUSES

(75) Inventors: Joe D. Sauer, Baton Rouge, LA (US);
George W. Cook, Jr., Baton Rouge, LA (US); Christopher S. Knight, Prairieville, LA (US)

(73) Assignee: Albemarle Corporation, Baton Rouge, LA (US)

( * ) Notice: Subject to any disclaimer, the term of this patent is extended or adjusted under 35 U.S.C. 154(b) by 72 days.

(21) Appl. No.: 12/513,288

(22) PCT Filed: Nov. 5, 2007

(86) PCT No.: PCT/US2007/083581
§ 371 (c)(1),
(2), (4) Date: May 1, 2009

(87) PCT Pub. No.: WO2008/058052
PCT Pub. Date: May 15, 2008

(65) Prior Publication Data
US 2010/0056479 A1 Mar. 4, 2010

(51) Int. Cl.
*A01N 33/12* (2006.01)
*A01N 33/00* (2006.01)
*C09D 5/18* (2006.01)

(52) U.S. Cl. .............. 514/642; 504/158; 106/18.13

(58) Field of Classification Search .......... None
See application file for complete search history.

(56) References Cited

U.S. PATENT DOCUMENTS

| | | | |
|---|---|---|---|
| 2,976,307 A | 3/1961 | Rudner et al. | |
| 3,169,983 A | 2/1965 | Hunter | |
| 3,660,459 A | 5/1972 | Hughes | |
| 4,613,373 A | 9/1986 | Umeno et al. | |
| 4,970,201 A | 11/1990 | Giebeler et al. | |
| 5,077,098 A | 12/1991 | Chow et al. | |
| 5,304,237 A | 4/1994 | Barth et al. | |
| 5,438,034 A | 8/1995 | Walker | |
| 5,641,726 A | 6/1997 | Walker et al. | |
| 5,700,841 A | 12/1997 | Walker et al. | |
| 5,855,804 A | 1/1999 | Walker et al. | |
| 5,891,921 A | 4/1999 | Walker et al. | |
| 6,080,789 A | 6/2000 | Lutz | |
| 2006/0257578 A1 | 11/2006 | Zhang et al. | |
| 2007/0148431 A1 * | 6/2007 | Sauer et al. | 428/292.4 |

FOREIGN PATENT DOCUMENTS

| | | |
|---|---|---|
| DE | 479016 | 7/1929 |
| EP | 0 370 182 | 5/1990 |
| RU | 2156268 | 9/2000 |
| WO | WO 94/28715 | 12/1994 |
| WO | WO 9428715 A1 * | 12/1994 |
| WO | WO 02/01958 | 1/2002 |
| WO | WO 02/081159 | 10/2002 |
| WO | WO 2005/097729 | 10/2005 |

* cited by examiner

*Primary Examiner* — Sreeni Padmanabhan
*Assistant Examiner* — Svetlana Ivanova
(74) *Attorney, Agent, or Firm* — Marcy M. Hoefling

(57) ABSTRACT

The present invention relates to the use of quaternary ammonium compounds in the remediation of microbial growth such as mold, funguses, and mildew.

1 Claim, No Drawings

USE OF QUATERNARY AMMONIUM COMPOUNDS IN THE REMEDIATION OF MOLD, MILDEW, AND FUNGUSES

FIELD OF THE INVENTION

The present invention relates to the use of quaternary ammonium compositions in the remediation of articles contaminated with mold, fungus, and mildew.

BACKGROUND OF THE INVENTION

It has been presented and discussed on numerous occasions that certain molds, mildews, and/or funguses pose a health hazard to many individuals, and the issue of remediation of such organisms is a constant problem in the construction industry. In particular, certain buildings and locations within buildings lend themselves to more readily promote or facilitate the growth of funguses, molds, and/or mildews, e.g. basements, crawl spaces, etc. Further, depending upon the particular type of building, and the particular geographic area in which the building is found, these buildings may provide suitable environments for fungal and/or microbial growth. For instance, spaces that are not adequately ventilated and/or exposed to moisture can contribute to growth of mold/microbes, and in some instances in new construction, some spaces are often not ventilated until final steps in the construction, allowing mold to grow and colonize at unacceptable levels, and the mold may quickly spread to other areas within the building. Further, with the recent hurricanes in South Louisiana, the issue of mold, fungus, and mildew remediation has become of more interest to those whose homes, buildings, etc, were flooded.

Current methods to remediate these organisms typically involve an oxidizing compound such as chlorine, peroxide, etc. While these oxidizing remediation measures can be effective; by their very nature, oxidizing compounds are not persistent, and are "spent" or "consumed" in a rapid fashion, leaving the system unprotected with regard to biocidal action. While oxidizing remediation compounds are not the only means of providing for remediation, most other remediation techniques are expensive and/or structurally intrusive. In some cases, it may even be necessary to remove and replace construction materials that have been sufficiently invaded with the mold or microbe.

Therefore, as the need for remediation continues, there constantly exists a need in the art for effective means of providing remediation for buildings, articles, etc. that have such mold/microbial problems.

Quaternary ammonium compounds or "quats" for short find use in many industrial applications. Quats are loosely defined as a group of compounds generally having the formula $R_1R_2R_3R_4-N^+Y^-$, where the radicals may be the same, different, or part of a ring and Y is a counter anion. Typically, but not always, one of the radicals is a long-chain alkyl group. In most industrial applications, these quat molecules are complexed with a counter ion (anion) to provide for an "active" molecule.

The inventors hereof have discovered that the use or application of a solution comprising a quaternary ammonium compound can provide for an effective, non-oxidizing remediation tool. In some embodiments, the application of this solution can also impart to the material, article, etc., to which it is applied some flame retardant properties. In some embodiments, when the quaternary ammonium compound in the solution has its counter anion borate, as described below, the application of the solution can also impart to the one or more articles some termite repellant properties. In this embodiment, the one or more articles to which the solution is applied must obviously be susceptible to termite damage, i.e. cellulosic substrates such as wood, cotton, paper, or bagasse-based building products. Non-limiting examples of these products include ceiling tiles, wooden furniture, wallboards, etc., and the like. By repelling termites, it is meant that the termites do not feed on the quat treated cellulosic material, and in essence may resort to cannibalistic behavior for food or search for a different food source, if one is available, instead of feeding on the quat treated cellulosic material as a food-source.

Thus, in one embodiment, the present invention relates to a method for remediation. The method comprises applying to one or more articles a quaternary ammonium compound having the formula:

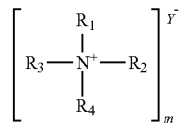

wherein Y is selected from $H_2BO_3^-$; $HBO_3^{-2}$; $BO_3^{-3}$; $B_4O_7^{-2}$; $HB_4O_7^-$; $B_3O_5^-$; $B_5O_8^{-2}$; $BO_2^-$; $PO_4^{-3}$; $HPO_4^{-2}$, $H_2PO_4^-$, $P_2O_7^{-4}$, $P_3O_{10}^{-5}$, $PO_3^-$; $CO_3^{-2}$; $HCO_3^-$; $[CO_2^-]_n R_5$; and combinations thereof; $P_1$, $R_2$, $R_3$ and $R_4$ are independently-selected from i) substituted or unsubstituted alkyl groups or it) substituted or unsubstituted alkenyl groups, wherein if i) or ii) is substituted, they have one or more substituent groups selected from aryl, heterocyclyl, hydroxyl, ester, benzyl, carboxyl, halo, nitro, cyano, alkoxy or oxo groups; and m is 1, 2, 3, 4, or 5, depending on the selection of Y; and wherein said one or more articles comprises at least one microbial.

DETAILED DESCRIPTION OF THE INVENTION

"Microbial", "microbe" and "microbial organism" can be used interchangeably herein and are used herein in the broadest sense and are meant to include one or more of the following: molds, mildews, funguses, and the like. In some embodiments, the microbial is considered a contaminant to the one or more article(s)

Also, "building" as used herein is also used in its broadest sense and is meant to include homes, office and/or other commercial buildings, storage units or buildings, apartments, mobile homes, travel trailers, detached garages, camps, and the like.

Articles Sought to be Remediated

In some embodiments, the article to be remediated is a construction material. Construction material is used herein in its broadest sense and is meant to encompass any material used in the construction of homes, and buildings upon which microbial organisms can grow. Thus, "construction material" as used herein is meant to encompass to wood, cotton, cardboard, liner board, other similar paper products, composite assemblies, cement, and the like. In some embodiments, the article can be any one of the following: i) gypsum board; ii) ceiling tiles or other ceiling material made form natural or synthetic materials; iii) particleboard or other similar composite material used in the construction of a building, i.e. fiber board, press-board, and the like; iv) synthetic wood, i.e. synthetic doors molded from resin materials, synthetic moldings, etc; v) carpeting; vii) padding used under carpeting; viii) insulation, be it made from natural or synthetic materials; ix)

wood; x) concrete or other similar porous material; xi) porous tiles such as flooring or wall tiles; xii) synthetic materials used in the construction of buildings, i.e. artificial marbles, stones, resins such as fiberglass, etc; xiii) bricks; and ix) any combinations thereof.

It can also be used in the remediation of "household" articles that are susceptible to contamination by unwanted microbials. Thus, in some embodiments, the material sought to be remediated is an article selected from one or more of the following: curtains, bed sheets, furniture (sofas, chairs, tables, beds, and the like), appliances (refrigerators, washing machines, microwave ovens, stoves, dryers, etc.), and the like.

Quaternary Ammonium Compound

The term "quaternary ammonium compound" and "quat", as used herein, refers to a compound having the general formula $R_1R_2R_4$—$N^+Y^-$, where the radicals may be the same, different, or part of a ring and Y is a counter anion. The organic radicals can be alkyl or alkenyl (unsaturated alkyls) groups that are linear or branched, substituted or unsubstituted, or mixtures thereof. The term "quaternary ammonium compound" or "quat" is also intended to encompass a compound in which one of the four organic radicals of a quat may be a "shared" radical with a second quat.

Generally, the quaternary ammonium compounds used in the present invention have the formula:

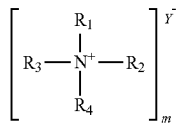

wherein Y is a counter-anion and m can be 1, 2, 3, 4, or 5, depending on the selection of Y.

The counter-anion of the quaternary ammonium compounds, Y, used in the present invention can be selected from borate anions, phosphate anions, carbonate anions ($CO_3^{-2}$), bicarbonate anions ($HCO_3^-$), and carboxylate anions ($[CO_2^-]_n\, R_5$). Thus, in some embodiments, Y is a borate anion, or a phosphate anion, or a bicarbonate anion, or a carbonate anion or a carboxylate anion. In the case where two quaternary ammonium compounds are present, it is preferred that the counter anion of one of the quats is a bicarbonate anion and/or a carbonate anion, or a phosphate anion or a carboxylate anion, and the counter anion of the other quaternary ammonium compound is a borate anion.

Borate anions suitable for use herein include the dihydrogen borate anion, $H_2BO_3^-$; the hydrogen borate anion, $HBO_3^{-2}$; the borate anion, $BO_3^{-3}$; the tetraborate anion, $B_4O_7^{-2}$; the hydrogen tetraborate anion, $HB_4O_7^-$; $B_3O_5^-$; pentaborate, $B_5O_8^{-2}$; and $BO_2^-$. Thus, Y is suitably selected from $H_2BO_3^{-3}$; $HBO_3^{-2}$; $BO_3^{-3}$; $B_4O_7^{-2}$; $HB_4O_7^-$; $B_3O_5^-$; $B_5O_8^{-2}$; and $BO_2^-$. If Y is a borate anion, it is preferred that Y is $BO_3^{-3}$, and m is 3.

Phosphate anions suitable for use herein include the phosphate anion, $PO_4^{-3}$; the hydrogen phosphate anion, $HPO_4^{-2}$; the dihydrogen phosphate anion, $H_2PO_4^{-3}$; the diphosphate anion, $P_2O_7^{-4}$, and the triphosphate anion, $P_3O_{10}^{-5}$. Thus, Y is suitably selected from $PO_4^{-3}$ $HPO_4^{-2}$, $H_2PO_4^-$, $P_2O_7^{-4}$, $P_3O_{10}^{-5}$, and $PO_3^-$. If Y is a phosphate anion, it is preferred that Y is $PO_4^{-3}$, and m is 3.

Carboxylate anions suitable for use herein have the general formula $[CO_2^-]_nR_5$, wherein n is an integer equal to or greater than 1 and $R_5$ is chosen from substituted, unsubstituted, saturated, or unsaturated alkyl groups containing in the range of from 1 to 25 carbon atoms. In some preferred embodiments, $R_5$ contains in the range of from about 10 to about 20 carbon atoms, in some embodiments in the range of from 10 to 12 carbon atoms, in other embodiments in the range of from 12 to 14 carbon atoms, in other embodiments in the range of from 12 to 14 carbon atoms, in other embodiments in the range of from 14 to 16 carbon atoms, and in still other embodiments in the range of from 16 to 18 carbon atoms.

In some embodiments, the quats used in the present invention are metal coupler free. By metal coupler free, it is meant that the quats do not contain metals such as copper, mercury, lead, cadmium, hexavalent chromium, arsenic, antimony, or zinc. These metals are commonly used for their biocidal properties. However, these and other "heavy" metals pose certain environmental concerns, thus, it would be beneficial to remediate articles without the use of these heavy metals.

The four carbon chains, i.e. $R_1$, $R_2$, $R_3$ and $R_4$, of the quats used in the present invention are independently selected from i) substituted or unsubstituted alkyl groups or ii) substituted or unsubstituted alkenyl groups, wherein if i) or ii) is substituted, they have one or more substituent groups selected from aryl, heterocyclyl, hydroxyl, ester, benzyl, carboxyl, halo, nitro, cyano, alkoxy or oxo groups. Alkyl and alkenyl groups suitable for use in the quats are those that contain in the range of from 1 to 20 carbon atoms. In preferred embodiments, $R_1$ and $R_2$ are independently chosen from alkyl groups having in the range of from 1 to 3 carbon atoms, and $R_3$ and $R_4$ are independently chosen in the range of from 6 to 20 carbon atom-containing groups selected from i) substituted or unsubstituted alkyl groups or ii) substituted or unsubstituted alkenyl groups, wherein if i) or ii) is substituted, they have one or more substituent groups selected from aryl, heterocyclyl, hydroxyl, ester, benzyl, carboxyl, halo, nitro, cyano, alkoxy or oxo groups; and m is 1, 2, or 3. In a more preferred embodiment, $R_1$ and $R_2$ are methyl groups and $R_3$, and $R_4$ are independently selected from unsubstituted alkyl groups containing in the range of from 8 to 14 carbon atoms. In one embodiment, one of $R_3$ or $R_4$ is an unsubstituted alkyl group containing in the range of from 8 to 10 carbon atoms, and one of $R_3$ or $R_4$ is an unsubstituted alkyl group containing in the range of from 12 to 14 carbon atoms.

In other embodiments of the present invention, at least one, sometimes only one and in other embodiments only two, of the four carbon chains, i.e. $R_1$, $R_2$, $R_3$ and $R_{41}$ is selected from i) substituted or unsubstituted alkyl groups that contain from 13 to 16, sometimes 14 to 16, sometimes 14, carbon atoms or it) substituted or unsubstituted alkenyl groups that contain from 13to 16, sometimes 14 to 16, sometimes 14, carbon atoms, wherein if i) or ii) is substituted, they have one or more substituent groups selected from aryl, heterocyclyl, hydroxyl, ester, benzyl, carboxyl, halo, nitro, cyano, alkoxy or oxo groups. These carbon chains can be saturated or unsaturated, preferably unsubstituted. In these embodiments, it is particularly preferred to select unsaturated substituted or unsubstituted, preferably unsubstituted, alkyl groups containing from 13 to 16, sometimes 14 to 16, sometimes 14, carbon atoms. In these embodiments, at least two, in some embodiments only two, and in other embodiments three, of $R_1$, $R_2$, $R_3$ and $R_4$ are independently chosen from alkyl groups having from 1 to 4, sometimes 1 to 3, in some embodiments 2 to 4, carbon atoms. In these embodiments, it is also contemplated that one of $R_1$, $R_2$, $R_3$ and $R_4$ be selected from i) substituted or unsubstituted alkyl groups or ii) substituted or unsubstituted alkenyl groups, wherein if i) or ii) is substituted, they have one or more substituent groups selected from aryl, heterocyclyl, hydroxyl, ester, benzyl, carboxyl, halo, nitro, cyano, alkoxy or oxo groups. The alkyl and alkenyl groups, are those that contain from 1 to 20 carbon atoms. In preferred embodiments, the one of $R_1$, $R_2$, $R_3$ and $R_4$ is chosen from 6 to 20 carbon atom-containing groups selected from i) substituted or unsubstituted alkyl groups or ii) substituted or unsubstituted alkenyl groups, wherein if i) or ii) is substituted, they have one or nitro, cyano, alkoxy or oxo groups; and m is 1, 2, 3, 4, or 5, sometimes 1, 2, or 3. In some embodiments, it is selected from unsubstituted alkyl groups containing from 8 to 14 carbon atoms. In other embodiments, it is selected from unsubstituted alkyl group containing from 8 to 10 carbon atoms, and in other embodiments, it is selected from unsubstituted alkyl groups containing from 12 to 14 carbon atoms.

In some embodiments of the present invention, it is preferred that at least two of the four carbon chains be independently selected chosen from alkyl groups having from 1 to 4, sometimes 1 to 3, in some embodiments 2 to 4, carbon atoms, and two of the four carbon chains be independently chosen from 6 to 20 carbon atom-containing groups selected from i) substituted or unsubstituted alkyl groups or ii) substituted or unsubstituted alkenyl groups, wherein if i) or ii) is substituted, they have one or more substituent groups selected from aryl, heterocyclyl, hydroxyl, ester, benzyl, carboxyl, halo, nitro, cyano, alkoxy or oxo groups; and m is 1, 2, 3, 4, or 5, sometimes 1, 2, or 3, wherein ranges as described above are contemplated and the two of the four carbon chains independently chosen from 6 to 20 carbon atom-containing groups contain different numbers of carbon atoms.

In another embodiment, m is 2, and one of the four organic radicals of a quat may be a "shared" radical with a second quat. It should be noted that while in this embodiment $R_4$ is shown as the shared radical, the shared radical can be any of $R_1$, $R_2$, $R_3$, or $R_4$. In this embodiment, the quaternary ammonium compounds used in the practice of the present invention have the general formula:

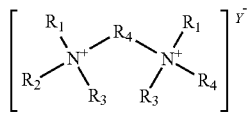

In this embodiment, $R_1$, $R_2$, $R_3$, and $R_4$ are as described herein including preferred embodiments, and Y is selected from those anions described above having an ionic charge of −2, in some embodiments a borate anion having an ionic charge of −2, in some embodiments, $HBO_3^{-2}$.

In another embodiment when m is 2, and one of the four organic radicals of a quat may be a "shared" radical with a second quat, the quaternary ammonium compounds used in the present invention have the general formula:

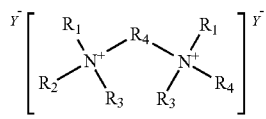

In this embodiment, $R_1$, $R_2$, $R_3$, $R_4$ are as described above including preferred embodiments, and each Y is independently selected from those anions described above having an ionic charge of −1, in some embodiments from borate anions having an ionic charge of −1, in other embodiments each Y is $H_2BO_3^-$. It should be noted that while in this embodiment $R_4$ is shown as the shared radical, the shared radical can be any of $R_1$, $R_2$, $R_3$, or $R_4$.

In another embodiment m is 3, and one of the four organic radicals of a quat is a "shared" radical with a second quat. In this embodiment, the quaternary ammonium compounds used in the coating formulations of the present invention can have the general formula:

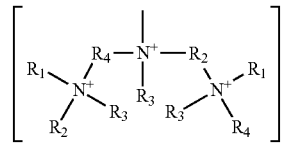

In this embodiment, $R_1$, $R_2$, $R_3$, and $R_4$ are as described herein including preferred embodiments, and one Y is independently selected from the counter-anions described above having an ionic charge of −2 and the other Y is selected from those counter-anions having an ionic charge of −1. In some embodiments, one Y is selected from $H_2BO_3^-$; $HB_4O_7^-$; $B_3O_5^-$; and $BO_2^-$ and the other Y is selected from $HBO_3^{-2}$; $B_4O_7^{-2}$; and $B_5O_8^{-2}$. It should be noted that while in this embodiment $R_4$ is shown as the shared radical, the shared radical can be any of $R_1$, $R_2$, $R_3$, or $R_4$.

In another embodiment when m is 3, and one of the four organic radicals of a quat may be a "shared" radical with a second quat, the quaternary ammonium compounds used in the present invention have the general formula:

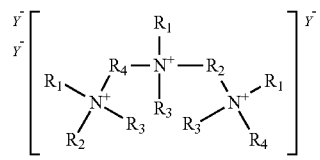

In this embodiment, $R_1$, $R_2$, $R_3$, and $R_4$ are as described above including preferred embodiments, and each Y is independently selected from those anions having a net ionic charge of −1. In some embodiments, each Y is independently selected from $H_2BO_3^-$; $HB_4O_7^-$; $B_3O_5^-$. It should be noted that while in this embodiment $R_4$ is shown as the shared radical, the shared radical can be any of $R_1$, $R_2$, $R_3$, or $R_4$.

In some embodiments, m is 3 and Y is $BO_3^{-3}$. In these embodiments, the quaternary ammonium compounds used in the present invention have the general formula:

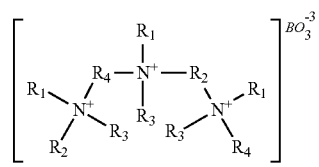

In this embodiment, $R_1$, $R_2$, $R_3$, or $R_4$ are as described above including preferred embodiments. It should be noted that while in this embodiment $R_4$ and $R_2$ are shown as the shared radicals, the shared radicals can be independently any of $R_1$, $R_2$, $R_3$, or $R_4$ or any combinations thereof. For example, $R_4$ and $R_1$ can be the shared radicals, $R_1$ and $R_3$ can be the shared radicals, etc. Also, all-three nitrogen atoms can share the same radical group, independently selected from $R_1$, $R_2$, $R_3$, or $R_4$.

The quats of the present invention can be prepared by any methods known in the art, exemplary-methods include those described in commonly-owned co-pending application PCT US2005/010162.

Solutions Containing the Quaternary Ammonium Compound

While the quat(s) can be applied to the one or more articles directly, it is preferred to apply a solution, in some embodiments an aqueous solution, in other embodiments an aqueous remediation solution, comprising the quat(s) to the one or more articles.

The processes used in the production of quats, for example those described in commonly-owned co-pending application PCT US2005/010162, typically produce quats in an aqueous solution. The aqueous solution typically comprises water, at least one polar organic co-solvent, and one or more quats, as described herein. Polar organic co-solvents present in these aqueous solutions typically have some compatibility with water since water is typically a component of the aqueous solution. Polar organic co-solvents are typically selected from several classes of compounds, such as: alcohols, such as methanol, ethanol, isopropyl alcohol, propanol, butanol, isobutyl alcohol, $C_1$-$C_6$ alcohols, $C_1$-$C_4$ alcohols; and the like, with methanol being a preferred example; polyalcohols, such as ethylene glycol, propylene glycol, and the like; esters, such as ethyl acetate, propyl acetate, formates, and the like; ethers, such as methyl tert-butyl ether, dioxane, glymes, and the like; and carbonyl-containing solvents, such as acetone, acetaldehyde, and the like. It should be noted that in some embodiments, only one polar organic co-solvent is used, and in other embodiments, more than one, sometimes two, or in other embodiments more that two, polar organic co-solvents are used.

These aqueous solutions generally have a polar organic co-solvent to water ratio in the range of from about 10:90 up to about 99:1 (wt. co-solvent: wt. water based on the combination of the water and polar organic co-solvent), and the exact amount of the polar organic co-solvent and water is selected according to the selection of $R_1$, $R_2$, $R_3$ and $R_4$. In general, it is preferred that the ratio of co-solvent:water, by weight and on the same basis, is within the range of from about 50:50 to about 99:1, about 60:40 to about 99:1 is more preferred, about 70:30 to about 98:2 is even more preferred, and about 80:20 to about 95:5 is yet more preferred.

It has generally been found that aqueous solutions having a higher ratio of cosolvent to water are preferred for quats containing very hydrophobic alkyl substituent groups, e.g., double tailed or twin tailed quats where the alkyl groups are $C_{10}$-$C_{20}$, for example, while aqueous solutions having a lower ratio of co-solvent to water are preferred for boron-quats having less hydrophobic alkyl substituent groups, e.g., a ($C_2$-$C_6$) alkyltrimethylammonium salt.

The aqueous solutions can contain as the polar organic co-solvent an alcohol, and thus, the aqueous solution comprises a mixture of alcohol and water. In this embodiment, it is typically preferred that the aqueous solution comprises a mixture of a $C_1$-$C_6$ alcohol and water in a ratio of from 10:90 to 99:1, by weight, on the same basis as above. Even more preferred is an aqueous solution that comprises a mixture of a $C_1$-$C_4$ alcohol and water in a ratio of from about 50:50 to about 99:1, about 60:40 to about 99:1 is more preferred, about 70:30 to about 98:2 is even more preferred, and about 80:20 to about 95:5 is yet more preferred, all by weight and on the same basis. A preferred aqueous solution used in the production of quat(s) is a mixture of methanol and water in a ratio of about 85:15, by weight, based on the water and alcohol.

It should be understood that the aqueous solutions can comprise water, at least one polar organic co-solvent and the quat(s). However, when describing the amount of water and polar organic co-solvent in the aqueous solution, these ratios were based on the amount of polar organic co-solvent and water. Thus, when considering the amounts of these components and the quat in the solution, the mixture is a ternary composition comprising at least three major components, water, polar organic co-solvent, and the quat(s) "salt". Thus, the ratio of the components of the aqueous solution can be represented as a ratio of wt. quat:wt. polar organic co-solvent: wt. water, based on the aqueous solution. By way of example, an aqueous solution formed by adding 25% by weight of a quat salt to a mixture comprising an 85:15 by weight mixture of methanol: water, would have a ternary composition, by weight, of 25:64:11, quat salt: methanol: water by weight, based on the aqueous solution.

Because of economic and/or process considerations these aqueous solutions generally have a concentration of quat(s) ranging from about 1 to about 50 wt. % quat, based on the aqueous solution. If the quat concentration of the aqueous solution is in the range of from about 1 to about 10 wt. %, based on the aqueous solution, then the aqueous solutions can be applied to the one or more articles as is, but these aqueous solutions are generally only available with quat concentrations in the range of from about 10 to about 30 wt. %, based on the aqueous-solution, of the quat(s), more typically in the range of from about 20 to about 30 wt. %, on the same basis. The inventors hereof have discovered that quat(s) concentrations this high are not necessary for remediating the one or more articles to which they are applied and ranges much lower are effective and less costly. Thus, in the practice of the present invention, a diluent can be added to the aqueous solution to form a remediation solution, obviously comprising the diluent and the about 1 to about 10 wt. %, in some embodiments in the range of from about 2 to about 8 wt. %, and in some embodiments in the range of about 4 to about 6 wt. %, all based on the remediation solution. Diluents suitable for use herein can be selected from polar organic co-solvents, as described above, water, and mixtures thereof. In some embodiments, the diluent is water.

Alternative Quaternary Ammonium Compounds

In some embodiments, one, in some embodiments more than one, quaternary ammonium compound(s) having the structure can be used:

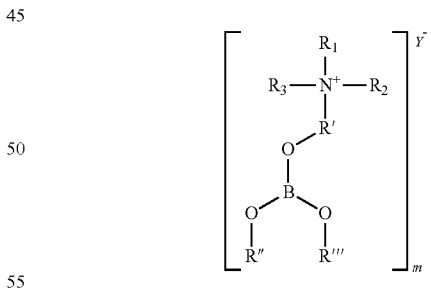

wherein $R_1$, $R_2$, $R_3$, Y, and m are as described above, R' is a hydrocarbon group having from 1-10 carbon atoms, in some embodiments in the range of from 1 to 5, in some embodiments in the range of from 1 to 3, and R" and R'" are independently selected from 1) substituted or unsubstituted alkyl groups or ii) substituted or unsubstituted alkenyl groups, wherein if i) or ii) is substituted, they have one or more substituent groups selected from aryl, heterocyclyl, hydroxyl, ester, benzyl, carboxyl, halo, nitro, cyano, alkoxy or oxo groups. In some embodiments R" and R'" are selected from unsubstituted alkyl groups having in the range of from 1 to 20 carbon atoms, in some embodiments in the range of from 1 to 15, and in other embodiments in the range of from 6 to 14.

In another embodiment, a first and second quaternary ammonium compound are used in the practice of the present invention. The first quaternary ammonium compound can have any of the formulas described above, but in some embodiments the first quaternary ammonium compound be characterized by the formula:

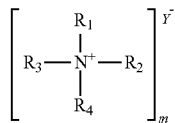

wherein the first quaternary ammonium composition is metal coupler free, m is as described above, and Y is selected from borates, as described above including preferred embodiments. In this embodiment, the four carbon groups; i.e., $R_1$, $R_2$, $R_3$ and $R_4$, of the first quaternary ammonium-compound are selected from those described above, including preferred embodiments.

In this embodiment, the second quaternary ammonium compound can have any of the formulas described above included preferred embodiments, but it is preferred that the second quaternary ammonium compound be characterized by the formula:

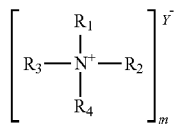

wherein the second quaternary ammonium composition is metal coupler free, m is as described above, and Y is selected from a counter-anion other than borate, in some embodiments carbonates and/or bicarbonates. In this embodiment, the four carbon groups, i.e., $R_1$, $R_2$, $R_3$ and $R_4$, of the first quaternary ammonium compound are selected from those described above, including preferred embodiments.

It is within the scope of the present invention that when Y of the second quaternary ammonium compound is bicarbonate or carbonate, that a third quaternary ammonium compound this embodiment, the third quaternary ammonium compound is metal coupler free, and the four carbon groups, i.e., $R_1$, $R_2$, $R_3$ and $R_4$, of the third quaternary ammonium compound are selected from those described above. In this embodiment, the Y counter-anion of the third quaternary ammonium compound is bicarbonate or carbonate, but not the same as the second quaternary ammonium compound For example, if Y of the second quaternary ammonium compound is carbonate, then Y of the third quaternary ammonium compound is bicarbonate, and vice versa.

Remediation of Article

In the remediation of the article, the quaternary ammonium compound, be it in solution or otherwise, is applied to the one or more article, and the method by which it is applied is not critical to the present invention. Non-limiting examples of suitable application methods include coating, dipping, soaking, brushing, spraying, pressure treating, and the like. Because of the nature of most remediation, it is preferred that the quaternary ammonium compound be applied through spraying, in some embodiments with a pressure spraying device such as a pressure washer or pressurized spraying system, e.g. a garden sprayer pressurized by hand pumping.

The above description is directed to several embodiments of the present invention. Those skilled in the art will recognize that other embodiments, which are equally effective, could be devised for carrying out the spirit of this invention. The present invention includes, without limitation:

1. A method comprising applying to one or more article(s) a quaternary ammonium compound having the formula:

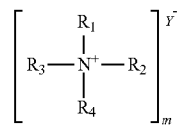

wherein Y is selected from $H_2BO_3^-$; $HBO_3^{-2}$; $BO_3^{-3}$; $B_4O_7^{-2}$; $HB_4O_7^-$; $B_3O_5^-$; $B_5O_8^{-2}$ $BO_2^-$; $PO_4^{-3}$, $HPO_4^{-2}$, $H_2PO_4^-$, $P_2O_7^{-4}$, $P_3O_{10}^{-5}$, $PO_3^-$; $CO_3^{-2}$; $HCO_3^-$; $[CO_2^-]_n R_5$; and combinations thereof; $R_1$, $R_2$, $R_3$ and $R_4$ are independently selected from i) substituted or unsubstituted alkyl groups or ii) substituted or unsubstituted alkenyl groups, wherein if i) or ii) is substituted, they have one or more substituent groups selected from aryl, heterocyclyl, hydroxyl, ester, benzyl, carboxyl, halo, nitro, cyano, alkoxy or oxo groups; n is an integer equal to or greater than 1 and $R_5$ is chosen from substituted, unsubstituted, saturated, or unsaturated alkyl groups containing in the range of from 1 to 25 carbon atoms; and m is 1, 2, 3, 4, or 5, depending on the selection of Y; and wherein said one or more article(s) comprises at least one microbial.

2. The method according to claim 1 wherein said quaternary ammonium compound is metal coupler free.

3. The method according to claim 1 wherein said one or more article(s) is any one of the following: i) gypsum board; ii) ceiling tiles or other ceiling material made, form natural or synthetic materials; iii) particleboard or other similar composite material used in the construction of a building; iv) synthetic wood; v) carpeting; vii) padding used under carpeting; viii) insulation, be it made from natural or synthetic materials; ix) wood; x) concrete or other similar porous material; xi) porous tiles such as flooring or wall tiles; xii) synthetic materials used in the construction of buildings; xiii) bricks; xiv) curtains; xv) bed sheets; xvi) furniture; xvii) appliances; xviii) wall paneling; and xix) any combinations thereof.

4. The method according to claim 3 wherein said quaternary ammonium compound is applied to said one or more article(s) by applying an aqueous or remediation solution containing in the range of from about 1 to about 10 wt. %, based on the aqueous or remediation solution, of said quaternary ammonium compound, to said one or more article.

5. The method according to claim 4 wherein said quaternary ammonium compound is applied to said one or more article(s) by a method selected from coating, dipping, soaking, brushing, spraying, and the like 6. The method according to claim 5 wherein $R_1$ and $R_2$ are independently chosen from alkyl groups having in the range of from 1 to 3 carbon atoms, and $R_3$ and $R_4$ are independently chosen from 6 to 20 carbon atom-containing groups selected from i) substituted or unsubstituted alkyl groups or ii) substituted or unsubstituted alkenyl groups, wherein if i) or ii) is substituted, they have one or more substituent groups selected from aryl, heterocyclyl, hydroxyl, ester, benzyl, carboxyl, halo, nitro, cyano, alkoxy or oxo groups.

7. The method according to claim 6 wherein $R_1$ and $R_2$ are methyl groups and $R_3$ and $R_4$ are independently selected from unsubstituted alkyl groups containing from 8 to 14 carbon atoms;

8. The method according to claim 7 wherein the carbon atom containing group of $R_3$ has a different number of carbons than the carbon atom containing group of $R_4$.

9. The method according to claim 6 wherein one of $R_3$ or $R_4$ is an unsubstituted alkyl group containing in the range of from 8 to 10 carbon atoms, and one of $R_3$ or $R_4$ is an unsubstituted alkyl group containing in the range of from 12 to 16 carbon atoms.

10. The method according to claim 6 wherein one of $R_3$ or $R_4$ is an unsubstituted alkyl group containing from 8 to 10 carbon atoms, and one of $R_3$ or $R_4$ is an unsubstituted alkyl group containing in the range of from 12 to 14 carbon atoms.

11. The method according to any of claims 1, or 5-10 wherein Y is $BO_3^{-3}$, and m is 3.

12. The method according to any of claims 1, or 5-10 wherein at least one of $R_1$, $R_2$, $R_3$, and $R_4$ is a shared radical.

13. The method according to claim 12 wherein i) m is 2, and ii) Y is selected from $HBO_3^{-2}$; $B_4O_7^{-2}$; and $B_5O_8^{-2}$.

14. The method according to claim 12 wherein i) m is 3, ii) said quaternary ammonium compound contains 2 shared anions Y, and iii) one of the shared anions is selected from $H_2BO_3^-$; $HB_4O_7^-$; $B_3O_5^-$; and $BO_2^-$ and the other shared anion is selected from $HBO_3^{-2}$; $B_4O_7^{-2}$; and $B_5O_8^{-2}$.

15. The method according claim 12 wherein i) m is 3, and ii) said quaternary ammonium compound contains 3 shared anions Y, each Y independently selected from $H_2BO_3^-$; $HB_4O_7^-$; $B_3O_5^-$; and $BO_2^-$.

16. The method according to claim 5 wherein said at least one quaternary ammonium compound has the formula:

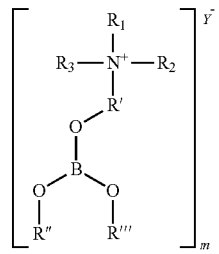

wherein Y is selected from $H_2BO_3^-$; $HBO_3^-$; $BO_3^{-3}$; $B_4O_7^{-2}$; $HB_4O_7^-$; $B_3O_5^-$; $B_5O_8^{-2}$; $BO_2^-$; $PO_4^{-3}$, $HPO_4^{-2}$, $H_2PO_4^-$, $P_2O_7^{-4}$, $P_3O_{10}^{-5}$, $PO_3^-$; $CO_3^{-2}$, $HCO_3^-$; $[CO_2^-]_nR_5$; and combinations thereof; $R_1$, $R_2$, $R_3$ and $R_4$ are independently selected from i) substituted or unsubstituted alkyl groups or ii) substituted or unsubstituted alkenyl groups, wherein if i) or ii) is substituted, they have one or more substituent groups selected from aryl, heterocyclyl, hydroxyl, ester, benzyl, carboxyl, halo, nitro, cyano, alkoxy or oxo groups; n is an integer equal to or greater than 1 and $R_5$ is chosen from substituted, unsubstituted, saturated, or unsaturated alkyl groups containing in the range of from 1 to 25 carbon atoms; and m is 1, 2, 3, 4, or 5, depending on the selection of Y; R' is a hydrocarbon group having from 1-10 carbon atoms; and R" and R''' are independently selected from i) substituted or unsubstituted alkyl groups or ii) substituted or unsubstituted alkenyl groups, wherein if i) or ii) is substituted, they have one or more substituent groups selected from aryl, heterocyclyl, hydroxyl, ester, benzyl, carboxyl, halo, nitro, cyano, alkoxy or oxo groups.

17. The method according to claim 5 wherein a first, second, and optionally a third, quaternary ammonium compound are applied to said one or more article(s) wherein a) said first quaternary ammonium compound is characterized by the formula:

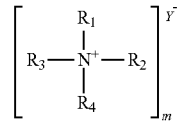

wherein said first quaternary ammonium compound is metal coupler free; Y is selected from $H_2BO_3^-$; $HBO_3^{-2}$; $BO_3^{-3}$; $B_4O_7^{-2}$; $HB_4O_7^-$; $B_3O_5^-$; $B_5O_8^{-2}$; and $BO_2^-$; $R_1$, $R_2$, $R_3$ and $R_4$ are independently selected from i) substituted or unsubstituted alkyl groups or ii) substituted or unsubstituted alkenyl groups, wherein if i) or ii) is substituted, they have one or more substituent groups selected from aryl, heterocyclyl, hydroxyl, ester, benzyl, carboxyl, halo, nitro, cyano, alkoxy or oxo groups; and m is 1, 2, 3, 4, or 5, depending on the selection of Y; and b) said second quaternary ammonium compound is characterized by the formula:

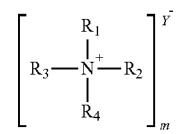

wherein said second quaternary ammonium compound is metal coupler free; Y is selected from $PO_4^{-3}$, $HPO_4^{-2}$, $H_2PO_4^-$, $P_2O_7^{-4}$, $P_3O_{10}^{-5}$, $PO_3^-$; $CO_3^{-2}$; $HCO_3^-$; $[CO_2^-]_nR_5$; and combinations thereof; $R_1$, $R_2$, $R_3$ and $R_4$ are independently selected from i) substituted or unsubstituted alkyl groups or ii) substituted or unsubstituted alkenyl groups, wherein if t) or it) is substituted, they have one or more substituent groups selected from aryl, heterocyclyl, hydroxyl, ester, benzyl, carboxyl, halo, nitro, cyano, alkoxy or oxo groups; and m is 1, 2, 3, 4, or 5, depending on the selection of Y.

18. The method according to claim 17 wherein each $R_1$ and $R_2$ of said first and second quaternary ammonium compound is independently chosen from alkyl groups having in the range of from 1 to 3 carbon atoms, and each $R_3$ and $R_4$ of said first and second quaternary ammonium compounds are independently chosen from 6 to 20 carbon atom-containing groups selected from i) substituted or unsubstituted alkyl groups or ii) substituted or unsubstituted alkenyl groups, wherein if i) or ii) is substituted, they have one or more substituent groups selected from aryl, heterocyclyl, hydroxyl, ester, benzyl, carboxyl, halo, nitro, cyano, alkoxy or oxo groups.

19. The method according to claim 18 wherein $R_3$ of said first quaternary ammonium compound has a different number of carbons than $R_4$ of said first quaternary ammonium compound.

20. The method according to claim 19 wherein $R_3$ of said second quaternary ammonium compound has a different number of carbons than $R_4$ of said second quaternary ammonium compound.

21. The method according to any of claims 1-10 or 17-20 said one or more article(s) is a cellulosic article and the application of said at least one quaternary ammonium compound imparts to said one or more article(s) termite repellant and/or flame retardant properties.

22. The method according to any of claims 1, 3, or 5-9 wherein said one or more article(s) is used for or in the construction of a building and said at least one quaternary ammonium compound is applied to said one or more article(s) at any stage, during the construction of said building.

23. The method according to claim 22 wherein said one or more article is a part of or present in an existing building.

24. The method according to any of claims 17-20, wherein said optional third quaternary ammonium compound is applied to said one or more article-along with said first and second quaternary ammonium compound; the counter anion Y of said second quaternary ammonium compound is $CO_3^{-2}$; and the third quaternary ammonium compound is characterized by the formula:

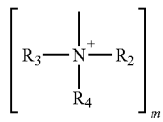

wherein said third quaternary ammonium compound is metal coupler free; Y is selected from $HCO_3^-$; $R_1$, $R_2$, $R_3$ and $R_4$ are independently selected from i) substituted or unsubstituted alkyl groups or ii) substituted or unsubstituted alkenyl groups, wherein if i) or it) is substituted, they have one or more substituent groups selected from aryl, heterocyclyl, hydroxyl, ester, benzyl, carboxyl, halo, nitro, cyano, alkoxy or oxo groups; and m is 1.

25. The method according to 24 wherein $R_3$ of said third quaternary ammonium compound has a different number of carbons than $R_4$ of said third quaternary ammonium compound.

26. The method according to claim 25 wherein said one or more article(s) is a cellulosic article and the application of said at least one quaternary ammonium compound imparts to said one or more article termite repellant and/or flame retardant properties.

27. The method according to claim 25 wherein said at least one quaternary ammonium compound is applied to said one or more article(s) at any stage during the construction of said building.

28. The method according to claim 25 wherein said one or more article(s) is a part of or present in an existing building.

29. A method comprising preventing and/or inhibiting the growth of microbial organism by applying to one or more article at least one quaternary ammonium compound having the formula:

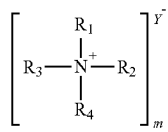

wherein said at least one quaternary ammonium compound is metal coupler free; Y is selected from $H_2BO_3^-$; $HBO_3^{-2}$; $BO_3^{-3}$; $B_4O_7^{-2}$; $HB_4O_7^-$; $B_3O_5^-$; $B_5O_8^{-2}$; $BO_2^-$; and combinations thereof; $R_1$ and $R_2$ are independently chosen from alkyl groups having in the range of from i to 3 carbon atoms; $R_3$ and $R_4$ are independently chosen from 6 to 20 carbon atom-containing groups selected from i) substituted or unsubstituted alkyl groups or ii) substituted or unsubstituted alkenyl groups, wherein if i) or ii) is substituted, they have one or more substituent groups selected from aryl, heterocyclyl, hydroxyl, ester, benzyl, carboxyl, halo, nitro, cyano, alkoxy or oxo groups; and m is 1, 2, or 3, depending on the selection of Y; and wherein said one or more article(s) comprises at least one microbial selected from one or more molds, mildews, funguses, and the like.

30. The method according to claim 29 wherein said one or more article(s) is any one of the following: i) gypsum board; ii) ceiling tiles or other ceiling material made form natural or synthetic materials; iii) particleboard or other similar composite material used in the construction of a building; iv) synthetic wood; v) carpeting; vii) padding used under carpeting; viii) insulation, be it made from natural or synthetic materials; ix) wood; x) concrete or other similar porous material; xi) porous tiles such as flooring or wall tiles; xii) synthetic materials used in the construction of buildings; xiii) bricks; xiv) curtains; xv) bed sheets; xvi) furniture; xvii) appliances; xviii) wall paneling; and xix) any combinations thereof.

31. The method according to claim 29 wherein said quaternary ammonium compound is applied to said one or more article(s) by applying to said one or more article(s) an aqueous or remediation solution containing in the range of from about 1 to about 10 wt. %, based on the aqueous or remediation solution.

32. The method according to claim 31 wherein said quaternary ammonium compound is applied to said one or more article(s) by a method selected from coating, dipping, soaking, brushing, spraying, and the like 33. The method according to claim 31 wherein the carbon atom containing group of $R_3$ has a different number of carbons than the carbon atom containing group of $R_4$.

34. The method according to claim 32 wherein $R_1$ and $R_2$ are methyl groups and $R_3$ and $R_4$ are independently selected from unsubstituted alkyl groups containing from 8 to 14 carbon atoms.

35. The method according to claim 34 wherein the carbon atom containing group of $R_3$ has a different number of carbons than the carbon atom containing group of $R_4$.

36. The method according to claim 33 wherein one of $R_3$ or $R_4$ is an unsubstituted alkyl group containing in the range of from 8 to 10 carbon atoms, and one of $R_3$ or $R_4$ is an unsubstituted alkyl group containing in the range of from 12 to 16 carbon atoms.

37. The method according to claim 33 wherein one of $R_3$ or $R_4$ is an unsubstituted alkyl group containing from 8 to 10 carbon atoms, and one of $R_3$ or $R_4$ is an unsubstituted alkyl group containing in the range of from 12 to 14 carbon atoms 38. The method according to any of claims 29-37 wherein at least one of $R_1$, $R_2$, $R_3$, and $R_4$ is a shared radical.

39. The method according to claim 38 wherein i) m is 2, and ii) Y is selected from $HBO_3^{-2}$; $B_4O_7^{-2}$; and $B_5O_8^{-2}$.

40. The method according to claim 38 wherein i) m is 3, ii) said quaternary ammonium compound contains 2 shared anions Y, and iii) one of the shared anions is selected from $H_2BO_3^-$; $HB_4O_7^-$; $B_3O_5^-$; and $BO_2^-$ and the other shared anion is selected from $HBO_3^{-2}$; $B_4O_7^{-2}$; and $B_5O_8^{-2}$.

41. The method according claim 38 wherein i) m is 3, and ii) said quaternary ammonium compound contains 3 shared anions Y, each Y independently selected from $H_2BO_3^-$; $HB_4O_7^-$; $B_3O_5^-$; and $BO_2^-$ 42. The method according claim 38 wherein i) m is 3, and ii) Y is $BO_3^{-3}$.

43. The method according to any of claims 29-32 wherein a first, second, and optionally a third quaternary ammonium compound are applied to said one or more article(s) wherein
a) said first quaternary ammonium compound is characterized by the formula:

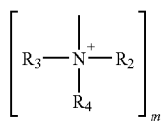

wherein said first quaternary ammonium compound is metal coupler free; Y is selected from $H_2BO_3^-$; $HBO_3^{-2}$; $BO_3^{-3}$; $B_4O_7^-$; $HB_4O_7^-$; $B_3O_5^-$; $B_5O_8^{-2}$; and $BO_2^-$; $R_1$, $R_2$, $R_3$ and $R_4$ are independently selected, from i) substituted or unsubstituted alkyl groups or ii) substituted or unsubstituted alkenyl groups, wherein if i) or ii) is substituted, they have one or more substituent groups selected from aryl, heterocyclyl, hydroxyl, ester, benzyl, carboxyl, halo, nitro, cyano, alkoxy or oxo groups; and, m is 1, 2, 3, 4, or 5, depending on the selection of Y; and b) said second quaternary ammonium compound is characterized by the formula:

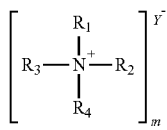

wherein said second quaternary ammonium composition is metal coupler free; Y is selected from $PO_4^{-3}$, $HPO_4^{-2}$, $H_2PO_4^-$, $P_2O_7^{-4}$, $P_3O_{10}^{-5}$, $PO_3^-$; $CO_3^{-2}$; $HCO_3^-$; $[CO_2^-]_n R_5$; and combinations thereof; $R_1$, $R_2$, $R_3$ and $R_4$ are independently selected from i) substituted or unsubstituted alkyl groups or ii) substituted or unsubstituted alkenyl groups, wherein if i) or ii) is substituted, they have one or more substituent groups selected from aryl, heterocyclyl, hydroxyl, ester, benzyl, carboxyl, halo, nitro, cyano, alkoxy or oxo groups; and m is 1, 2, 3, 4, or 5, depending on the selection of Y.

44. The method according to claim 43 wherein each $R_1$ and $R_2$ of said first and second quaternary ammonium compound is independently chosen from alkyl groups having in the range of from 1 to 3 carbon atoms, and each $R_3$ and $R_4$ of said first and second quaternary ammonium compounds are independently chosen from 6 to 20 carbon atom-containing groups selected from i) substituted or unsubstituted alkyl groups or ii) substituted or unsubstituted alkenyl groups, wherein if i) or ii) is substituted, they have one or more substituent groups selected from aryl, heterocyclyl, hydroxyl, ester, benzyl, carboxyl, halo, nitro, cyano, alkoxy or oxo groups.

45. The method according to claim 43 wherein $R_3$ of said first quaternary ammonium compound has a different number of carbons than $R_4$ of said first quaternary ammonium compound.

46. The method according to claim 45 wherein $R_3$ of said second quaternary ammonium compound has a different number of carbons than $R_4$ of said second quaternary ammonium compound.

47. The method according to any of claims 29-37 wherein said one or more article(s) is a cellulosic article and the application of said at least one quaternary ammonium compound imparts to said one or more article(s) termite repellant and/or flame retardant properties.

48. The method according to claim 43 wherein said one or more article(s) is a cellulosic article and the application of said at least one quaternary ammonium compound imparts to said one or more article termite repellant and/or flame retardant properties.

49. The method according to any of claims 29-37 wherein said one or more article is used for or in the construction of a building and said at least one quaternary ammonium compound is applied to said one or more article at any stage during the construction of said building.

50. The method according to claim 49 wherein said one or more article(s) is a part of or present in an existing building.

51. The method according to 38 wherein said one or more article(s) is used for or in the construction of a building and said at least one quaternary ammonium compound is applied to said one or more article(s) at any stage during the construction of said building.

52. The method according to claim 51 wherein said one or more article(s) is a part of or present in an existing building.

53. The method according to 43 wherein said one or more article(s) is used for the construction of a building and said at least one quaternary ammonium compound is applied to said one or more article(s) at any stage during the construction of said building.

54. The method according to claim 43 wherein said one or more article(s) is a part of or present in an existing building.

55. The method according to claim 43, wherein said optional third quaternary ammonium compound is applied to said one or more article(s) along with said first and second quaternary ammonium compound; the counter-anion Y of said second quaternary ammonium compound is $CO_3^{-2}$; and the third quaternary ammonium compound is characterized by the formula:

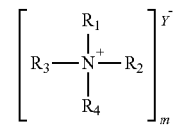

wherein said third quaternary ammonium composition is metal coupler free; Y is selected from $HCO_3^-$; $R_1$, $R_2$, $R_3$ and $R_4$ are independently selected from i) substituted or unsubstituted alkyl groups or ii) substituted or unsubstituted alkenyl groups, wherein if i) or ii) is substituted, they have one or more substituent groups selected from aryl, heterocyclyl, hydroxyl, ester, benzyl, carboxyl, halo, nitro, cyano, alkoxy or oxo groups; and m is 1.

56. The method according to 55 wherein $R_3$ of said third quaternary ammonium compound has a different number of carbons than $R_4$ of said third quaternary ammonium compound.

57. The method according to claim 56 wherein said one or more article(s) is a cellulosic article and the application of said at least one quaternary ammonium compound imparts to said one or more article(s) termite repellant and/or flame retardant properties.

58. The method according to claim 56 wherein said one or more article(s) is used for or in the construction of a building and said at least one quaternary ammonium-compound is applied to said one or more article(s) at any stage during the construction of said building.

59. The method according to claim 56 wherein said one or more article(s) is a part of or present in an existing building.

60. At least one article comprising at least one microbial wherein said at least one microbial is selected from one or more molds, mildews, funguses, and the like and at least one quaternary ammonium compound having the formula:

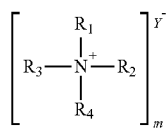

wherein Y is selected from $H_2BO_3^-$; $HBO_3^{-2}$; $BO_3^{-3}$; $B_4O_7^{-2}$; $HB_4O_7^-$; $B_3O_5^-$; $B_5O_8^{-2}$; $BO_2^-$; $PO_4^{-3}$; $HPO_4^{-2}$, $H_2P_4^-$, $P_2O_7^{-4}$, $P_3O_{10}^{-5}$, $PO_3^-$; $CO_3^{-2}$; $HCO_3^-$, $[CO_2^-]_nR_5$; and combinations thereof; $R_1$ and $R_2$ are independently chosen from alkyl groups having in the range of from 1 to 3 carbon atoms; $R_3$ and $R_4$ are independently chosen from 6 to 20 carbon atom-containing groups selected from i) substituted or unsubstituted alkyl groups or ii) substituted or unsubstituted alkenyl groups, wherein if i) or ii) is substituted, they have one or more substituent groups selected from aryl, heterocyclyl, hydroxyl, ester, benzyl, carboxyl, halo, nitro, cyano, alkoxy or oxo groups; n is an integer equal to or greater than 1 and $R_5$ is chosen from substituted, unsubstituted, saturated, or unsaturated alkyl groups containing in the range of from 1 to 25 carbon atoms; and m is 1, 2, or 3, depending on the selection of Y.

61. The at least one article according to claim 39 wherein said at least one article is selected from: i) gypsum board; ii) ceiling tiles or other ceiling material made form natural or synthetic materials; iii) particleboard or other similar composite material used in the construction of a building; iv) synthetic wood; v) carpeting; vii) padding used under carpeting; viii) insulation, be it made from natural or synthetic materials; ix) wood; x) concrete or other similar porous material; xi) porous tiles such as flooring or wall tiles; xii) synthetic materials used in the construction of buildings; xiii) bricks; xiv) curtains; xv) bed sheets; xvi) furniture; xvii) appliances; xviii) wall paneling; and xix) any combinations thereof.

62. The at least one article according to claim 40 wherein the carbon atom containing group of $R_3$ has a different number of carbons than the carbon atom containing group of $R_4$.

63. The at least one article according to claim 40 wherein $R_1$ and $R_2$ are methyl groups and $R_3$ and $R_4$ are independently selected from unsubstituted alkyl groups containing from 8 to 14 carbon atoms.

64. The at least one article according to claim 42 wherein the carbon atom containing group of $R_3$ has a different number of carbons than the carbon atom containing group of $R_4$.

65. The at least one article according to claim 40 wherein one of $R_3$ or $R_4$ is an unsubstituted alkyl group containing in the range of from 8 to 10 carbon atoms, and one of $R_3$ or $R_4$ is an unsubstituted alkyl group containing in the range of from 12 to 16 carbon atoms.

66. The at least one article according to claim 40 wherein one of $R_3$ or $R_4$ is an unsubstituted alkyl group containing from 8 to 10 carbon atoms, and in other embodiments, and one of $R_3$ or $R_4$ is an unsubstituted alkyl group containing in the range of from 12 to 14 carbon atoms.

What is claimed:

1. A method of remediation of one or more article(s) contaminated with microbial organisms, comprising applying to the articles a quaternary ammonium compound having the formula:

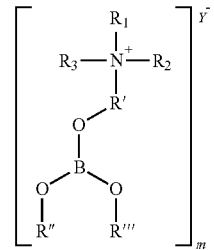

wherein Y is selected from $B_4O_7^{-2}$; $HB_4O_7^-$; $B_3O_5^-$; $B_5O_8^{-2}$; $BO_2^-$; and combinations thereof; $R_1$, $R_2$, and $R_3$ are independently selected from i) substituted or unsubstituted alkyl groups or ii) substituted or unsubstituted alkenyl groups, wherein if i) or ii) is substituted, they have one or more substituent groups selected from aryl, heterocyclyl, hydroxyl, ester, benzyl, carboxyl, halo, nitro, cyano, alkoxy or oxo groups; m is 1, 2, 3, 4, or 5, depending on the selection of Y; R' is a hydrocarbon group having from 1-10 carbon atoms; and R" and R'" are independently selected from i) substituted or unsubstituted alkyl groups or ii) substituted or unsubstituted alkenyl groups, wherein if i) or ii) is substituted, they have one or more substituent groups selected from aryl, heterocyclyl, hydroxyl, ester, benzyl, carboxyl, halo, nitro, cyano, alkoxy or oxo groups; and wherein said quaternary ammonium compound is applied to said one or more article(s) by a method selected from coating, dipping, soaking, brushing, or spraying.

* * * * *